US 6,616,649 B1

(12) United States Patent
Ismail

(10) Patent No.: US 6,616,649 B1
(45) Date of Patent: Sep. 9, 2003

(54) COMBINATION OF UNDERWEAR AND AN ABSORBENT PAD

(75) Inventor: Zubeir Ismail, Leicester (GB)

(73) Assignee: Milords International Limited of Hamiliton House, Leicester (GB)

( * ) Notice: Subject to any disclaimer, the term of this patent is extended or adjusted under 35 U.S.C. 154(b) by 0 days.

(21) Appl. No.: 09/445,115

(22) PCT Filed: Apr. 1, 1999

(86) PCT No.: PCT/GB99/01018

§ 371 (c)(1),
(2), (4) Date: Feb. 22, 2000

(87) PCT Pub. No.: WO99/51177

PCT Pub. Date: Oct. 14, 1999

(30) Foreign Application Priority Data

Apr. 4, 1998 (GB) .............................................. 9807200

(51) Int. Cl.⁷ ............................................... A61F 13/15
(52) U.S. Cl. ........................................ 604/393; 604/402
(58) Field of Search ................... 604/385.01, 385.14, 604/385.16, 386, 389, 393, 395, 396, 387, 390, 391, 385.04, 394, 398, 399, 400, 402, 397, 401; 2/406, 408

(56) References Cited

U.S. PATENT DOCUMENTS

| 1,426,525 A | | 8/1922 | Walsh | |
| 3,088,462 A | * | 5/1963 | Muto | 604/369 |
| 3,208,454 A | * | 9/1965 | Farkas | 2/408 |
| 3,224,448 A | * | 12/1965 | Diebold | 2/401 |
| 3,747,602 A | * | 7/1973 | Ralph | 604/398 |
| 3,749,095 A | | 7/1973 | Toyama | |
| 4,560,381 A | * | 12/1985 | Southwell | 2/406 |
| 4,568,341 A | * | 2/1986 | Mitchell et al. | 604/368 |
| 4,637,078 A | | 1/1987 | Southwell | |
| 5,011,480 A | * | 4/1991 | Gossens et al. | 604/385.23 |
| 5,201,727 A | * | 4/1993 | Nakanishi et al. | 604/358 |
| 5,241,710 A | * | 9/1993 | Lockhart | 2/406 |
| 5,325,543 A | * | 7/1994 | Allen | 2/406 |
| 5,368,585 A | | 11/1994 | Dokken | |
| 5,388,275 A | * | 2/1995 | Oram | 2/400 |
| 5,401,268 A | * | 3/1995 | Rodier | 604/383 |
| 5,415,650 A | * | 5/1995 | Sigl | 604/385.03 |
| 5,429,633 A | * | 7/1995 | Davis et al. | 604/385.04 |
| 5,562,648 A | | 10/1996 | Peterson | |
| 5,584,829 A | * | 12/1996 | Lavash et al. | 604/385.04 |
| 5,651,779 A | | 7/1997 | Burrell | |
| 5,772,648 A | * | 6/1998 | Osborn, III | 604/385.1 |
| 5,827,261 A | * | 10/1998 | Osborn, III et al. | 604/387 |

FOREIGN PATENT DOCUMENTS

| GB | 966718 | 8/1964 |
| GB | 1495744 | 12/1977 |
| WO | WO 85/03430 A1 | 8/1985 |

\* cited by examiner

Primary Examiner—Weilun Lo
Assistant Examiner—Michele Kidwell
(74) Attorney, Agent, or Firm—Marshall, Gerstein & Borun

(57) ABSTRACT

In combination an item of underwear (10) including a front part (11), a back part (12), a waist part (13) and a crotch part (14) which in use extends front to back between the legs of a wearer and a sanitary pad (30) of the kind having side wings (34) which carry an adhesive, characterised in that the item of underwear includes an inside lining part (20) which extends over at least a substantial portion of the crotch part (14) and has sides (25,26) which are unattached to the crotch part (14) over at least part of the front to back extent of the crotch part (14), and the side wings (34) of the pad are foldable into a position between the crotch part (14) of the item (10) and the inside lining part (20) with the adhesive adhered to the inside lining part (20).

10 Claims, 3 Drawing Sheets

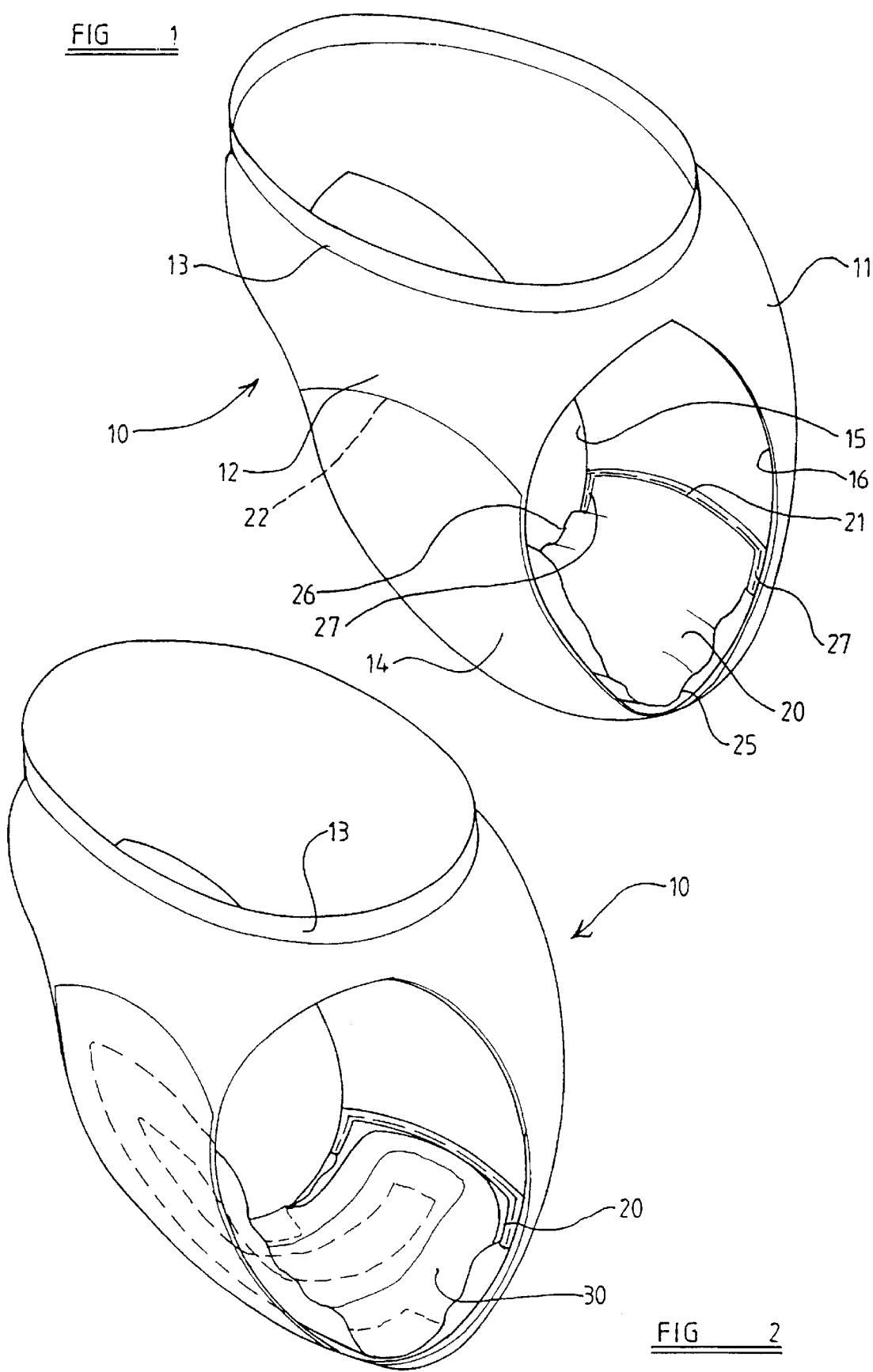

COMBINATION OF UNDERWEAR AND AN ABSORBENT PAD

DESCRIPTION OF INVENTION

This invention relates to an item of underwear worn in combination with a sanitary pad of the kind which extends between the legs of a wearer over at least a pail of the crotch.

Such sanitary pads are, for example, used by women during menstruation.

Conventionally such sanitary pads are maintained in position by virtue of being adhered to the wearer's underwear by an adhesive which is applied to the sanitary pad and exposed by the removal of a protective sheet. However because such adhesive cannot be so strong that the sanitary pad when soiled cannot be readily removed, such means for retaining the sanitary pad in use are not reliable.

To assist in retaining the sanitary pad in position, it is known to provide sides which conventionally are folded under the crotch part of the item of underwear and attached by an adhesive to the underside of the crotch part, but the wings can make the sanitary pad uncomfortable to wear.

According to a first aspect of the invention we provide in combination an item of underwear including a front part, a back part, a waist part and a crotch part which in use extends front to back between the legs of a wearer, and a sanitary pad of the kind having side wings which carry an adhesive, characterized in that the item of underwear includes an inside lining part which extends over at least a substantial portion of the crotch part had has sides which are unattached to the crotch part over at least part of the front to back extent of the crotch part, and the side wings of the sanitary pad are foldable into a position between the crotch part of the item and the inside lining part with the adhesive adhered to the inside lining part.

Thus the side wings are contained between the crotch part and the lining part, making a more comfortable arrangement. Additionally, the side wings, being located between the inside lining pail and the crotch pail, do not present unsightly lines visible through outer clothing.

Preferably the inside lining part extends over the entire crotch part from front to back and perhaps too, at least some of at least one of the front and backparts of the item.

For example, an item of underwear conventionally comprises a gusset provided by overlapping front and back pails, wvhich gusset forms the crotch part of the garment. Thus the inside lining pail may extend from front to back over a greater extent than such conventional gusset pail so that a sanitaly pad may be attached to the inside lining part over a substantial portion of its front to back length.

The inside lining part may comprise ends as well as sides. The sides may be shaped to conform generally to sides of the crotch part and preferably each extend outwardly beyond the sides of the crotch part but may be arranged not to extend outwardly beyond the sides of the crotch part if desired. The inside lining part may be attached to tlhe remainder of the item along the ends preferably by stitching. Additionally, tlhe inside lining pail may be attached to the remainder of the item, along pails only of the sides adjacent one or both of the ends so that the lining part is unattached to the crotch pail over at least a mid portion of the crotch part. Such additional attachment may provide for greater support for a sanitary pad attached to the inside lining pail.

Instead of or in addition to relying on adhesive to secure the sanitary pad to the item of underwear, if desired the inside lining part may be made of a looped material or a material presenting a plurality of hooks, with which loops or hooks, hooks or loops provided on the sanitary pad, in use, engage. mass of fibres with which a plurality of hooks provided on the sanitary pad, in use, engage.

Conveniently the plurality of hooks or loops are provided by a carrier material adhered to the sanitary pad, intermediate the side wings thereof.

For environmental reasons, preferably the carrier material or other means which present the plurality of hooks or loops is bio-degradable, so that a soiled sanitary pad may be disposed of by flushing.

For comfort, preferably the carrier material is flexible although it will be appreciated that a wearer would be isolated from the carrier material through the sanitary pad.

According to the second aspect of the invention we provide an item of underwear for use in the combination of the first aspect of the invention.

The invention will now be described with reference to the accompanying drawings in which:

FIG. 1 is an illustrative view of an item of underwear for use in a combination in accordance with the invention;

FIG. 2 is an illustrative view showing the item of FIG. 1 in combination with a sanitary pad:

Figure 3:
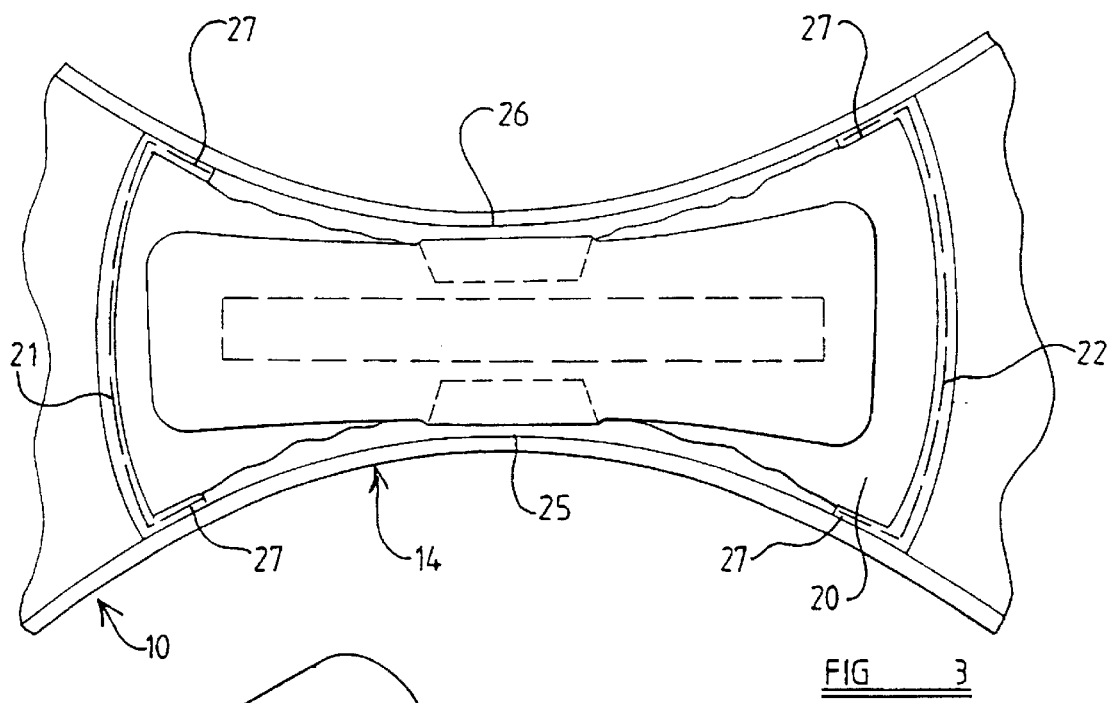
FIG. 3 is a more detailed plan view of the combination of FIG. 2.

Referring to the drawings there is shown an item of underwear 10 comprising a front part 11, a back part 12, which are connected to provide a waist part 13 and a crotch part 14, the crotch part 14 extending from front to back in use between a wearer's legs. The front 11 and back 12 parts provide openings 15, 16 for the wearer's legs and the crotch part 14 is provided by a elongate gusset of overlapping material of the front and back palrs 11, 12.

In accordance with the invention there is provided an inside lining part 20 which completely or substantially covers the crotch part 14 and extends to the front 11 and back 12 parts, where ends 21,22 of the inside lining part are each connected by a line of stitching, to the front 11 and back parts 12. The inside lining part 20 has sides 25,26 which extend front to back and which are configured generally to conform to the shapes of the usually elasticated, sides of the crotch part 14 but do not extend outwardly beyond the sides of the crotch part 14. In this example, portions 27 of the sides 25,26 of the inside lining part 20 are also connected by stitching to the crotch part 14 of the item 10, but the sides 25,26 of the inside lining part 20 are unattached along at least parts of the front to back extent for a purpose hereinafter explained.

In this example, the inside lining part 20 is made of a light brushed Nylon material, but may be made of another material which is adapted to co-operate with material presenting a plurality of hooks or loops such as felt, whereby the materials may become attached to one another.

In this example, where the inside lining part 20 is made of brushed Nylon, the material carrying the plurality of hooks may comprise Velcro (Registered Trade Mark) type material or at least the hooked material of Velcro fastenings.

Figure 4:
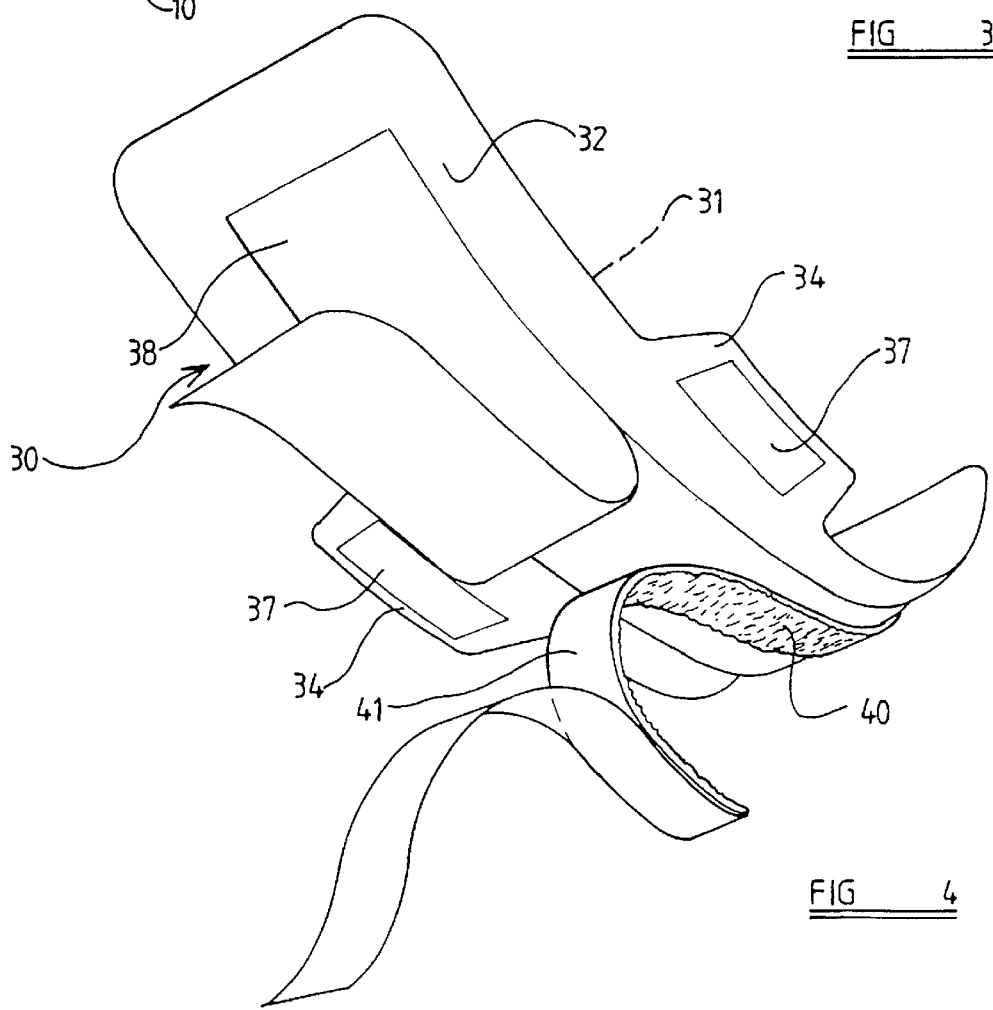
FIG. 4 is an illustrative view of a sanitaly pad which may be used with the item of FIG. 1 to provide the combination of FIG. 2.

Referring particularly to FIG. 4, a sanitary pad 30 of the kind used by women during menstruation is shown. The sanitary pad 30 comprises an absorbent surface 31 and a backing 32. The sanitary pad 30 is of the kind having side wings 34 which carry adhesive and conventionally are adapted to be folded beneath a crotch part of an item of underwear.

The backing 32 too comprises adhesive, the adhesive of the side wings 34 and the adhesive of the backing 32 being protected by protective sheets 37. 38 respectively, until required.

In this example, there is attached to the sanitary pad 30 a carrier material 40 in the form of a strip. The carrier material 40 preferably has its own adhesive, considerably stronger than the adhesive conventionally provided on the sanitary pad 30, the adhesive of the carrier material 40 strongly adhering the carrier material 40 to the backing 32 of the sanitary pad 30 once the protective sheet 38 of the sanitary pad 30 has been removed.

If desired the carrier material 40 may be provided to a consumer separately from the pad 30, with the adhesive of the carrier material 40 protected by a protective sheet 41 which is removed for use.

The carrier material 40 carries in this example a plurality of hooks and preferably is of (hooked) Velcro (Registered Trade Mark) type material. However the carrier material 40 is preferably flexible for comfort's sake, and is preferably a bio-degradable material so that the sanitary pad 30 with the carrier material 40 attached, is flushable.

Thus the pad 30 may be primarily attached to the item of underwear 10 shown in FIG. 1 with the plurality of hooks of the carrier material 40 engaging the brushed Nylon or other material of the inside lining part 20 so that the pad 30 becomes firmly attached to the inside lining part 20.

By virtue of the unattached side portions of the inside lining part 20, the side wings 34 may be folded between the inside lining part 20 and the crotch part 14 of the item of underwear (with the protective sheets 37 removed), and the adhesive thereon may adhere the side wings 34 to the underside of the inside lining part 20 for added security, and additionally, the wings 34 thus concealed, do not present unsightly lines in any outer garment, and are comfortably accommodated.

Various modifications may be made without departing from the scope of the invention.

For example, instead of the inside lining part 20 being made of brushed Nylon, or similar material, the part 20 may be made of another material which may co-operate with a plurality of hooks or loops provided by a sanitary pad 30. Thus the sanitaly pad 30, and/or carrier material 40 thereof may provide either a plurality of hooks or loops although hooks are preferred.

If desired, the sanitary pad 30 may be primarily secured to the lining part 20 by the adhesive usually provided on the sanitary pad 30, with the side wings 34 tucked under.

Figure 5:
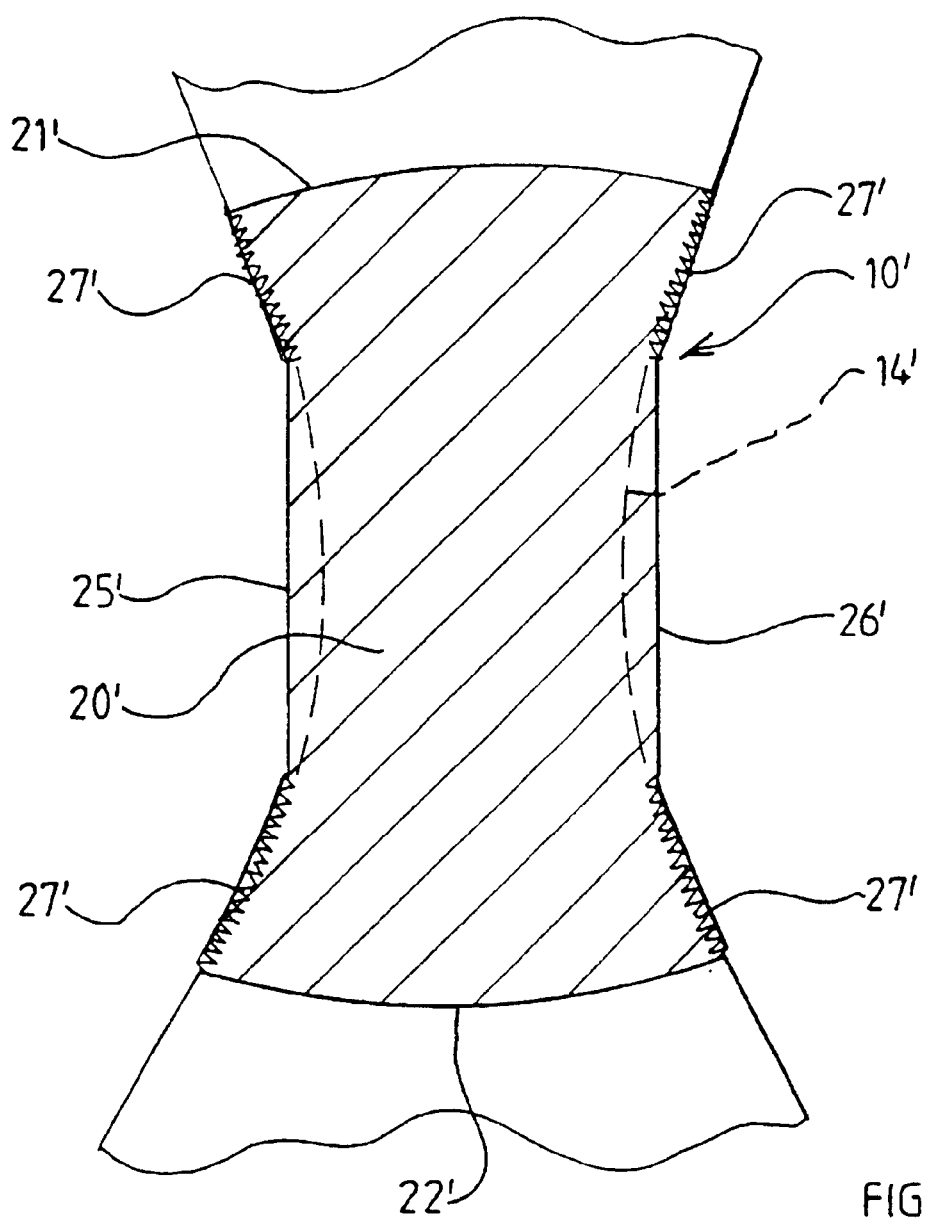
FIG. 5 is a plan view inside a modified item of underwear for use in a combination of the invention.

Referring to FIG. 5, part of a modified item of underwear 10' is illustrated. Similar parts to these in the preceding figures are labelled with the same reference numbers, with a prime sign added.

In this arrangement the sides 25', 26' of the inside lining part 20' again conform generally to the sides of the crotch part 14, but overlap the sides of the crotch part 14' slightly. Again portions 27' of the sides 25', 26' of the lining part 20' are connected by stitching the crotch part 14', with further potions between the stitched portions 27' being unattached to enable side wing 34 of the sanitaly pad to be fold under.

The sides of the crotch part 14' are generally elasticated, and the elasticated sides are less prone to soiling with the sides 25', 26' of the lining part 20' overlapping as shown.

Although the invention has been described particularly for use by women during menstruation, the invention may be used by an incontinent invalid for example. In any event, the item of underwear 10 may be worn with or without the sanitary pad 30, at least where the material of the inside lining part 20 is of brushed Nylon or similar comfortable material, when a sanitary pad is not required.

What is claimed is:

1. In combination an item of underwear including a front part, a back part, a waist part and a crotch part which in use extends front to back between a right leg and a left leg of a wearer and a sanitary pad of a kind having side wings which carry an adhesive, wherein the item of underwear includes an inside lining part which extends over at least a substantial portion of the crotch part and has sides which are unattached to the crotch part over at least part of a front to back extent of the crotch part and the inside lining part further including a first end adjacent the front part and a second end adjacent the back part, said sides being attached to the underwear only at locations adjacent at least one of said first end and said second end, and the side wings of the sanitary pad are folded into a position between the crotch part of the item of underwear and the inside lining part with the adhesive adhered to the inside lining part.

2. A combination according to claim 1 wherein the inside lining part extends over an entirety of the crotch part of the underwear from front to back.

3. A combination according to claim 1 wherein the crotch part includes crotch part sides, and the inside lining part includes ends in addition to the sides, the sides being shaped to conform generally to the crotch part sides but not outwardly beyond the crotch part sides, the inside lining part being attached to the item of underwear along the ends of the inside lining part.

4. A combination according to claim 3 wherein the inside lining part is attached to the item of underwear along parts of the sides of the inside lining part adjacent to one or both of the ends so that the inside lining part is unattached to the crotch part over at least a mid portion of the crotch part.

5. A combination according to claim 1 wherein the inside lining part is made of a looped material or a material presenting a plurality of hooks, with which loops or hooks, provided on the sanitary pad, in use, engage.

6. A combination according to claim 1 wherein the inside lining part is made of a brushed material which presents a mass of fibers with which a plurality of hooks provided on the sanitary pad, in use, engage.

7. A combination according to claim 5 wherein the plurality of hooks or loops are provided by a carrier material adhered to the sanitary pad intermediate the side wings thereof.

8. A combination according to claim 7 wherein the carrier material is biodegradable.

9. A combination according to claim 8 wherein the carrier material is flexible.

10. An item of underwear including a front part, a back part, a waist part, and a crotch part which in use extends front to back between the legs of a wearer, and an inside lining part which extends over at least a substantial portion of the crotch part and has sides which are unattached to the crotch part over at least part of the front to back extent of the crotch part and the inside lining part further including a first end adjacent the front part and a second end adjacent the back part, said sides being attached to the underwear only at locations adjacent at least one of said first end and said second end, a position between the crotch part and the inside lining part being adapted to receive side wings of a sanitary pad adhered to the inside lining part.

* * * * *